United States Patent
Alonso et al.

(10) Patent No.: US 9,793,178 B2
(45) Date of Patent: Oct. 17, 2017

(54) FOCUSED BEAM SCATTEROMETRY APPARATUS AND METHOD

(71) Applicants: Miguel A. Alonso, Rochester, NY (US); Stephen Head, Rochester, NY (US); Michael Theisen, Santa Rosa, CA (US); Thomas Brown, Rochester, NY (US)

(72) Inventors: Miguel A. Alonso, Rochester, NY (US); Stephen Head, Rochester, NY (US); Michael Theisen, Santa Rosa, CA (US); Thomas Brown, Rochester, NY (US)

(73) Assignee: University of Rochester, Rochester, NY (US)

( * ) Notice: Subject to any disclaimer, the term of this patent is extended or adjusted under 35 U.S.C. 154(b) by 37 days.

(21) Appl. No.: 14/833,540

(22) Filed: Aug. 24, 2015

(65) Prior Publication Data

US 2016/0061723 A1 Mar. 3, 2016

Related U.S. Application Data

(60) Provisional application No. 62/043,169, filed on Aug. 28, 2014.

(51) Int. Cl.
*H01L 21/66* (2006.01)
*G01B 11/22* (2006.01)
(Continued)

(52) U.S. Cl.
CPC ............... *H01L 22/12* (2013.01); *G01B 11/02* (2013.01); *G01B 11/22* (2013.01); *G01B 11/30* (2013.01);
(Continued)

(58) Field of Classification Search
CPC ......... H01L 21/67242; H01L 21/67253; H01L 21/67288; H01L 22/00; H01L 22/10;
(Continued)

(56) References Cited

U.S. PATENT DOCUMENTS 7,151,632 B2 * 12/2006 Biss ..................... G02B 27/283
  250/225
7,808,648 B2 * 10/2010 Sandstrom ............... G01J 4/04
  356/495

(Continued)

OTHER PUBLICATIONS

Davis et al.: "Encoding amplitude information onto phase-only filters" Allied Optics/vol. 38, No. 23/Aug. 10, 1999.
(Continued)

*Primary Examiner* — Gordon J Stock, Jr.
(74) *Attorney, Agent, or Firm* — Andrew J. Anderson, Esq.; Harter Secrest & Emery LLP

(57) ABSTRACT

The capacity to measure nanoscale features rapidly and accurately is of central importance for the monitoring of manufacturing processes in the production of computer integrated circuits. It is known that far-field scattered light requires a priori sample information in order to reconstruct nanoscale information such as is required in semiconductor metrology. Parameters of interest include, for example, trench depth, duty cycle, wall angle and oxide layer thickness. We describe a scatterometry apparatus and method that uses unconventional polarization states in the pupil of a high NA objective lens, and refer to this as focused beam scatterometry, in which the illumination consists of a focused field with a suitably tailored, spatially-varying polarization distribution. We describe how four or more parameters can be measured and distinguished with an accuracy consistent with the needs laid out in the semiconductor roadmap.

18 Claims, 5 Drawing Sheets

(51) Int. Cl.
*G01N 21/21* (2006.01)
*G01N 21/95* (2006.01)
*G01B 11/30* (2006.01)
*G01B 11/02* (2006.01)
*G03F 7/20* (2006.01)

(52) U.S. Cl.
CPC ......... *G01N 21/21* (2013.01); *G01N 21/9501* (2013.01); *G03F 7/70625* (2013.01); *G01B 2210/56* (2013.01)

(58) Field of Classification Search
CPC ......... H01L 22/12; H01L 22/20; H01L 22/24; H01L 22/26; H01L 22/30; G03F 7/70608; G03F 7/70616; G03F 7/70625; G03F 7/7065; G03F 7/70633; G03F 7/70641; G01B 9/04; G01B 11/02; G01B 11/022; G01B 11/024; G01B 11/028; G01B 11/03; G01B 11/06; G01B 11/0616; G01B 11/0625; G01B 11/0633; G01B 11/0641; G01B 11/065; G01B 11/16; G01B 11/168; G01B 11/22; G01B 11/24; G01B 11/26; G01B 11/30; G01B 11/303; G01B 11/306; G01N 21/21; G01N 21/211; G01N 21/214; G01N 21/47; G01N 21/4788; G01N 21/55; G01N 21/8422; G01N 21/88; G01N 21/8803; G01N 21/8806; G01N 21/9501; G01N 21/9503; G01N 21/9505; G01N 2021/4735; G01N 2021/4792; G01N 2021/8427; G01N 2021/8433; G01N 2021/8438; G01N 2021/8461

See application file for complete search history.

(56) References Cited

U.S. PATENT DOCUMENTS

| | | | | |
|---|---|---|---|---|
| 8,456,632 B2* | 6/2013 | Dainty | ...................... | G01J 4/04 356/364 |
| 8,582,114 B2* | 11/2013 | Manassen | ........... | G03F 7/70633 356/509 |
| 8,681,413 B2* | 3/2014 | Manassen | ............. | G01J 1/4257 359/237 |
| 9,474,143 B2* | 10/2016 | Zhan | ........................ | H05H 3/04 |
| 9,551,939 B2* | 1/2017 | Mathijssen | ........... | G06F 9/7069 |
| 2007/0091325 A1* | 4/2007 | Nikoonahad | .......... | G01B 11/24 356/625 |
| 2014/0358480 A1* | 12/2014 | Raquel | ............... | G01N 21/9501 702/184 |
| 2015/0323471 A1* | 11/2015 | Sapiens | .............. | G01N 21/9501 356/73 |
| 2016/0025646 A1* | 1/2016 | Manassen | .............. | G01N 21/47 356/369 |
| 2016/0025992 A1* | 1/2016 | Van Der Zouw | .. | G01N 21/8806 250/216 |

OTHER PUBLICATIONS

Maurer et al.: "Tailoring of arbitrary optical vector beams" New Journal of Physics 9 (2007).

Paz et al.: "Solving the inverse grating problem by white light interference Fourier scattreometry" Instute of Applied Optics (Apr. 24, 2012).

Peng et al.: "Efficient implementation of rigorous coupled-wave analysis for surface-relief gratings" J. Opt. Soc. Am. A 12, 1087-1096 (1995).

Lalanne et al.: "Highly improved convergence of the coupled-wave method for TM polarization" J. Opt. Soc. Am. A 13, 779-784 (1996).

Chateau et al.: "Algorithm for the rigorous coupled-wave analysis of grating diffraction" J. Opt. Soc. Am. A 11, 1321-1331 (1994).

Theisen et al.: "Amplitude, phase, and polarization control with a single spatial light modulator" Proc. SPIE 8949, 8949-69 (2014).

* cited by examiner

FIG. 3a)
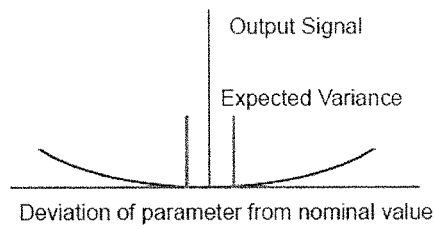
FIG. 3b)
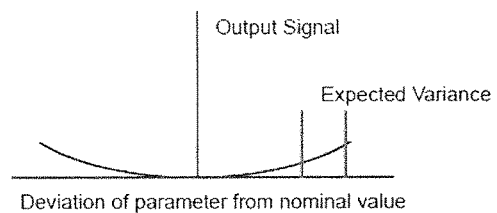
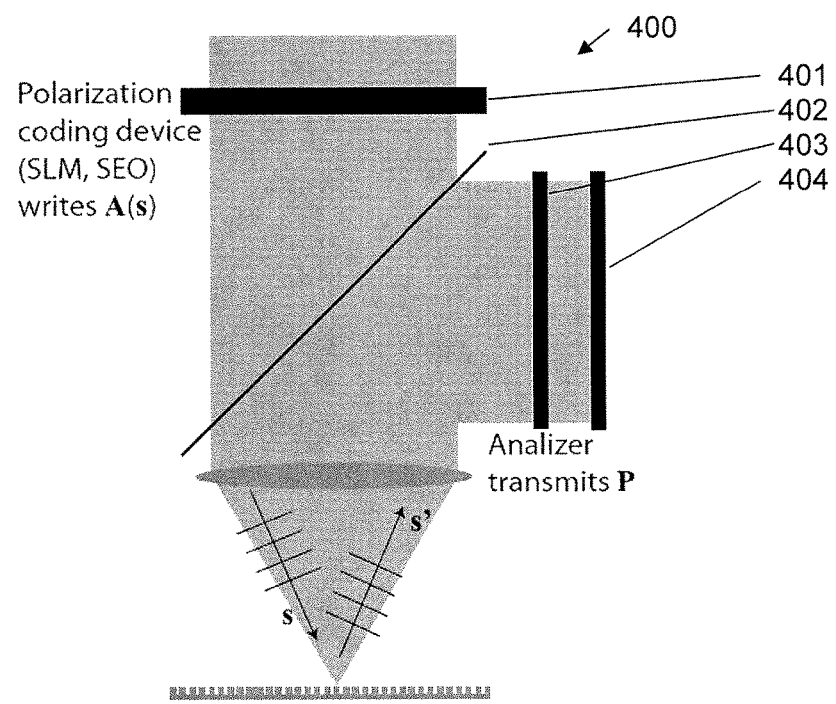
FIG. 4

FOCUSED BEAM SCATTEROMETRY APPARATUS AND METHOD

RELATED APPLICATION DATA

The instant application claims priority to U.S. provisional application Ser. No. 62/043,169 filed Aug. 28, 2014, the subject matter of which is incorporated by reference in its entirety.

BACKGROUND

Embodiments and aspects of the invention are generally directed to methods and associated apparatus for rapid and accurate nanoscale metrology. More particular embodiments and aspects are directed to methods and associated apparatus for rapidly and accurately measuring and/or characterizing nanoscale features of integrated circuits and the like. Most particularly, embodiments and aspects are directed to methods and associated apparatus using focused beam scatterometry for rapidly and accurately measuring and/or characterizing one or more nanoscale-related process errors of an object having a periodic or quasi-periodic structure such as, but not limited to, semiconductor metrology.

Accurate measurement of subnanometer features is central to the success of semiconductor fabrication. For most fabrication lines, inline process monitoring is essential to assuring that etch depths are accurate, side wall angles are within tolerance, coatings have the right thickness and composition, critical dimensions (CD) are accurate, and that line edge roughness is sufficiently small. For features smaller than 100 nm, direct imaging is usually not possible unless carried out in a scanning electron microscope. The measurements are therefore carried out with test targets whose features are similar to the circuit features but whose scattering properties can be predicted using numerical tools such as rigorous coupled wave analysis.

Scatterometry, involving the retrieval of a grating shape from the measurement of scattered light, has become the standard method for deducing nm-scale deviations from nominal values in semiconductor lithography. Most approaches to scatterometry have measured the scattering from oblique angles (and often over several wavelengths) in a sequential manner. The beam is usually brought to a slow (low NA) focus on a test target whose nominal dimensions are known; the results of the measurement are compared to a lookup table generated from a rigorous electromagnetic model.

A number of innovative extensions to conventional scatterometry have evolved in recent years. These have been aimed at features 22 nm and smaller, and are also driven by the need to measure the details of deep trench structures, and novel gate designs such as are found in Fin FET devices. Some reported approaches combined very precise optomechanical scanning with differential imaging or have explored phase-sensitive scatterometry using coherent light (e.g. digital holographic microscopy).

Scatterometry methods may be compared with conventional and spectroscopic ellipsometry. Ellipsometry is a model-based measurement method that combines rigorous electromagnetic theory with polarization control and analysis to decouple film thickness from the optical constants of the material. Micro-ellipsometry (in which the polarization over the pupil of a focusing lens is controlled and analyzed) allows ellipsometry to be carried out at very high spatial resolution but is generally limited to feature sizes larger than a wavelength.

The inventors have recognized the benefits and advantages in providing enabling solutions using polarization in the scatterometry of deeply subwavelength features that have known nominal values. These solutions enable optimizing the polarization distribution over the pupil in order to extract several process parameters in a single measurement. The embodied invention particularly advantageously enables the decoupling of multiple process errors using an off-null measurement method and apparatus.

DEFINITIONS AS USED HEREIN

The term 'about' means the amount of the specified quantity plus/minus a fractional amount (e.g., ±10%, ±9%, ±8%, ±7%, ±6%, ±5%, ±4%, ±3%, ±2%, ±1%, ±<1%, etc.) thereof that a person skilled in the art would recognize as typical and reasonable for that particular quantity or measurement.

The term 'substantially' means as close to or similar to the specified term being modified as a person skilled in the art would recognize as typical and reasonable; for e.g., within typical manufacturing and/or assembly tolerances, as opposed to being intentionally different by design and implementation.

SUMMARY

The most general aspects of the invention are a method and associated apparatus for rapid and accurate nanoscale metrology.

An aspect of the invention is a focused beam scatterometry method for characterizing an object having a periodic or quasi-periodic structure and one or more process errors. The method involves selecting a predictive scattering model for a perfectly specified test target of the object for providing predictive data; identifying one or more process error parameters of the object to be characterized; providing a focused light field input having at least a spatially varying polarization distribution over the field that will yield a particular functional form output for a respective one of the process errors, given a known polarization output analyzer; illuminating the object or a test target of the object with the input light field; collecting light scattered/reflected from the object or the test target of the object as measured data; and characterizing each of the identified one or more process error parameters in a single measurement by comparing the measured data with the predictive data. According to various exemplary, non-limiting embodiments, the method may include the following additional steps, features, limitations, and/or characteristics:

wherein the one or more process error parameters include a process error and a measurement range;
  further comprising selecting the spatially varying polarization distribution of the input light field that will yield a particular functional form output for at least two respective ones of the process errors;
  further comprising selecting the spatially varying polarization of the input light field that will yield a particular functional form output for at least four respective ones of the process errors;
  wherein the one or more process error parameters are selected from a group consisting of an etch depth, a side wall angle, a coating thickness, a coating composition, a line edge roughness, and a critical dimension of the object;
  wherein at least one of the one or more process error parameters has a scale less than 1000 nanometers;

wherein the at least one of the one or more process error parameters has a scale less than 22 nanometers;

wherein the input light field is in the form of a single focused beam comprising an ensemble of plane waves;

wherein each of the plane waves has an intensity, a polarization, and a phase characteristic, further wherein at least some of the waves' characteristics are different than at least some others of the waves' characteristics;

wherein collecting the light scattered/reflected from the object or the test target of the object comprises measuring an irradiance distribution of the scattered/reflected light over an exit pupil of a measurement system used for the measurement;

wherein the object is a semiconductor fabrication;

wherein the object is a Fin FET device;

further comprising collecting the measured data using an off-null methodology;

wherein the off-nulling conditions for the parameters are varied over the pupil of the system, such that the final irradiance distributions have shapes from which the error parameters can be inferred.

An aspect of the invention is a focused beam scatterometry apparatus/system for characterizing an object having a periodic or quasi-periodic structure and one or more process errors. In an embodiment, the apparatus/system includes an input light field polarization coding component; a focusing component for focusing the input light field on an object to be characterized, disposed in an optical path of the polarization coding component; a polarization analyzer component disposed to receive the input light field scattered/reflected from the object to be characterized; and a detector disposed to receive an output from the polarization analyzer. According to various exemplary, non-limiting embodiments, the apparatus/system may include the following additional components, assemblies, features, limitations, and/or characteristics:

wherein the input light field polarization coding component is a spatial light modulator (SLM);

wherein the polarization analyzer component is one of a linear polarizer and a circular polarizer;

wherein the apparatus/system is disposed/used in an off-null configuration.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE FIGURES

FIG. 3a, b schematically illustrate the differences between a) null measurements and b) off-null measurements.

FIG. 4 schematically illustrates in a cross sectional view a focused beam scatterometry apparatus/system, according to an illustrative aspect of the invention.

DETAILED DESCRIPTION OF NON-LIMITING, EXEMPLARY EMBODIMENTS

Figure 1:
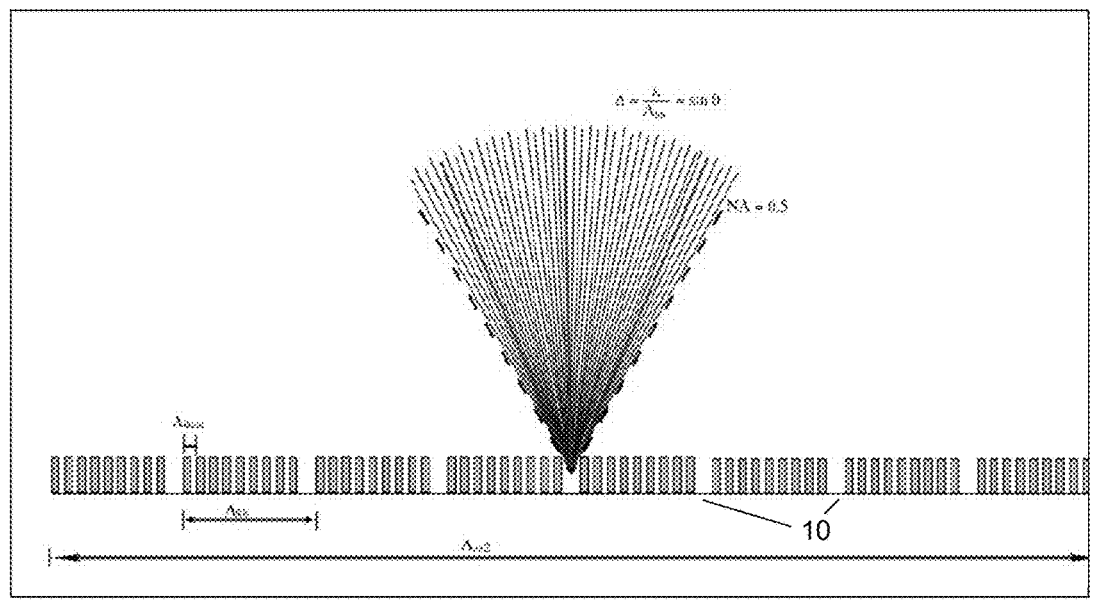
FIG. 1 schematically illustrates in a cross sectional view the principle of focused beam scatterometry.

The principle of focused beam scatterometry is illustrated in FIG. 1. It is based on the premise that any focal field may be represented as an ensemble of plane waves, each with a different direction. The plane waves may have different amplitudes (in the case of an amplitude apodized pupil), phase (in the case of an aberrated or phase-apodized pupil), or polarization. Reflected/scattered light then causes mixing between components of the angular spectrum in a way that is specifically influenced by the nanoscale features of the target. The goal of focused beam scatterometry is then to construct an input polarization distribution that optimizes the sensitivity to specific process parameters.

Figure 2:
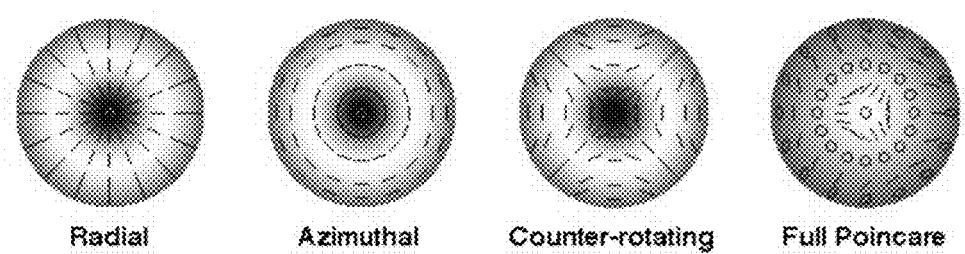
FIG. 2 schematically illustrates several examples of unconventional polarization states.
Figure 5A:
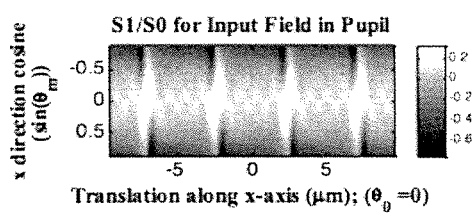
FIGS. 5a-c schematically illustrate polarization distribution across the pupil required for a null measurement as a function of sample translation.
Figure 5D:
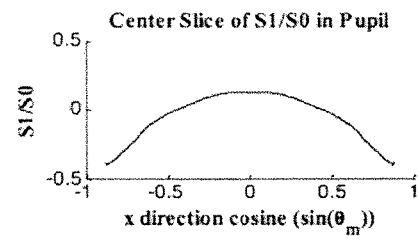
FIGS. 5d-f null polarization distribution when the sample is centered.
Figure 5B:
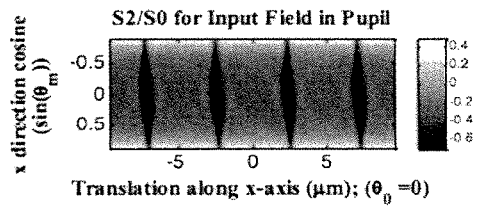
Figure 5E:
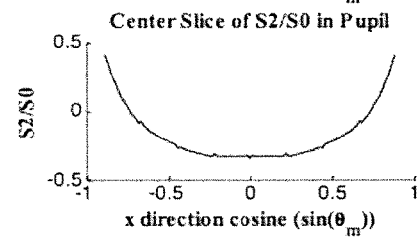
Figure 5C:
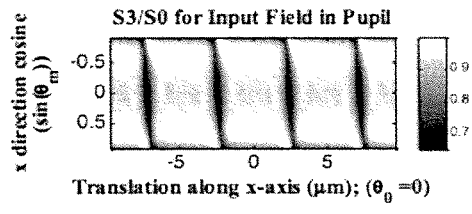
Figure 5F:
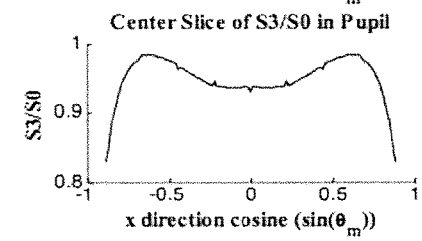

In the most general case, the illumination fields will have a space-variant polarization distribution. For the last twenty years, there has been considerable interest in the behavior of high numerical aperture systems whose illumination (pupil) fields depart from the textbook descriptions of uniformly polarized beams—these have often been referred to as unconventional polarization states. When applied to azimuthal and radial polarizations, they are sometimes termed polarization vortex beams or cylindrical vector beams. It is also possible to create beams in which every possible polarization state is included. Several examples of unconventional polarization states are shown in FIG. 2.

Null and Off-Null Measurements

Nulling is an important principle in polarization related measurements. Null ellipsometry, for example, seeks to find a combination of input polarization state and output analyzer that will zero a detector signal; precise knowledge of the input and output polarization states that produce the null condition can then allow one to deduce optical constants and thicknesses in a thin film stack. The null condition has the disadvantage that the signal itself is generally a quadratic function for small process errors, making it difficult to deduce the magnitude and/or sign of the error. In contrast, the off-null measurement seeks to linearize the problem while keeping the background signal small. FIG. 3 illustrates this principle, comparing the case of a null measurement (a) with an off-null measurement (b).

Optical Modeling

Scatterometry generally makes use of periodic and quasiperiodic structures. The gold standard for modeling these types of interactions is rigorous coupled wave analysis (RCWA). RCWA makes use of a layer-by-layer Fourier expansion of the dielectric function in a way that, in the limit of a large number of diffracted orders, boundary conditions can be precisely satisfied. During the 1990's, many papers were published that reported ways to improve the convergence of the method, especially for TM waves. Our numerical approach is that used by Peng and Morris, "Efficient implementation of rigorous coupled-wave analysis for surface-relief gratings." J. Opt. Soc. Am. A 12, 1087-1096 (1995), with improvements suggested by Lalanne and Morris, "Highly improved convergence of the coupled-wave method for TM polarization." J. Opt. Soc. Am. A 13, 779-784 (1996), the subject matters of which are incorporated by reference in their entireties. The formulation of the boundary condition is the same as that outlined by Chateau and Hugonin, "Algorithm for the rigorous coupled-wave analysis of grating diffraction." J. Opt. Soc. Am. A 11, 1321-1331 (1994), the subject matter of which is incorporated by reference in its entirety.

RCWA computes a complex reflection and transmission scattering matrix that connects the incident direction vector s with all transmitted and reflected orders of the grating. For example, in FIG. 1, the scattering from the coarse grating 10 (macropitch) will diffract light between the diffracted orders 12; the micropitch 11 will not couple to propagating orders but will induce interaction with evanescent fields.

To describe focused beam scatterometry, a scattering matrix must be assembled that samples the entire angular spectrum of the incident light for two orthogonal polarizations. In this way, any fully polarized input state may be formed as a (complex) linear combination of, for example, TE and TM input fields and be represented as an input vector A(s) that is multiplied by the scattering matrix $\check{R}(s',s)$ to yield the reflected amplitude, phase, and polarization at any given output direction s', $$R(s', s) = \begin{bmatrix} R_{11}(s', s) & R_{12}(s', s) \\ R_{21}(s', s) & R_{22}(s', s) \end{bmatrix}$$

where the subscripts denote scattering between and among TE (subscript 1) and TM (subscript 2) components, respectively. In general A(s) will represent an arbitrary polarization distribution; however, in operation of the embodied apparatus and method, we implement a smoothly varying polarization distribution(s) that optimizes the sensitivity and specificity of multiparameter measurements.

As illustrated n FIG. 1, distinction can be made between nm-scale features (the micropitch, 11) and micron-scale features (the macropitch, 10). In scatterometry, the distinction is important because a macropitch will induce scattering between any two propagating waves that coincide with diffraction orders. A micropitch induces only interaction with the evanescent fields but leaves the scattering matrix diagonal in (s,s'). Both types can induce coupling between different polarization components. FIG. 4 schematically illustrates the input and output polarization control in a focused beam scatterometry apparatus 400. The apparatus includes a polarization coding device 401 such as a spatial light modulator 'SLM' or stress-engineered optical element 'SEO'), a beam combiner 402 (e.g., beamsplitter; Wollaston prism and a hologram), a polarization analyzer 403 (e.g., oriented-linear polarizer; circular polarizer), and a detector 404.

Modeling a Null Measurement

The numerical procedure described above may be applied to the problem of a null measurement. We define a particular grating (that could be fabricated as a test target) that represents a perfectly specified nanostructure and define an input polarization state that will perfectly null the backscattering of a focused beam. For ordinary multilayers, this is a simple inverse problem. However, since the scattering matrix necessarily includes all of the evanescent fields, it is necessary to iteratively solve the inverse problem by first neglecting the evanescent interactions to estimate an initial field, and then include the evanescent fields in a forward computation. An example of this calculation is shown in FIG. 5(a-f); the polarization is adjusted for a null reflection using a −45 degree linear analyzer.

The illustrated results focus on in-plane modeling, in which we consider a cross-section of the pupil perpendicular to the grating lines. We take the fields to be fully polarized across the pupil and represent them in terms of the Stokes parameters S1 (difference between the irradiance of horizontal and vertically polarized light), S2 (the difference between plus and minus 45 degrees), and S3 (the difference between circular components). FIG. 5(a-c) show the polarizations necessary for a null condition as a function of sample translation. FIG. 5(d-f) show cross-sectional plots of the polarization distribution necessary for a null condition when the sample is perfectly centered. The results show that it is possible to define a smoothly varying polarization distribution in order to achieve a null condition and that all three Stokes parameters show significant variation across the pupil.

Optimizing the Polarization for Off-Null Measurements

Figure 6:
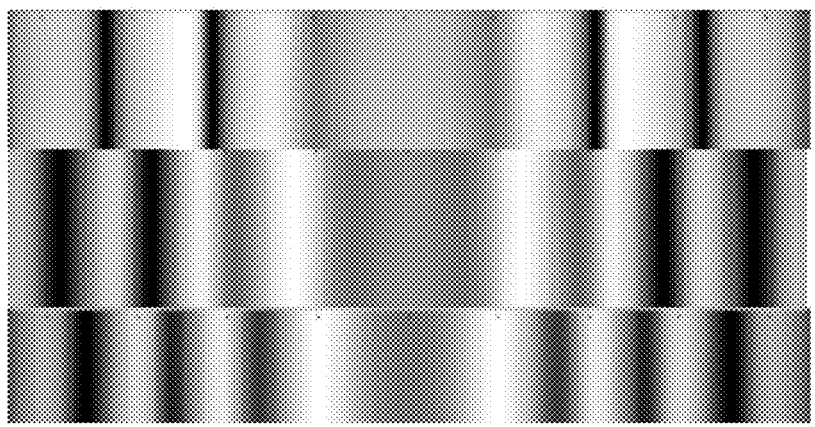
FIG. 6 illustrates predicted irradiance changes induced on the pupil in an off-null configuration for three different process errors, according to an illustrative aspect of the invention.

We now presume that the input state deviates from the null condition by a small amount and define an irradiance distribution across the pupil that shows sufficient changes in irradiance and form that would permit the quantitative determination of process parameters. As an example of this (FIG. 6), we consider an off-null configuration and compare the irradiance distribution across the pupil between process errors that represent a CD error, a sidewall angle error, and an error in oxide thickness. This suggests that it is possible to create an input polarization distribution that can produce irradiance patterns having different functional form depending on the particular process error.

The irradiance over the pupil (I(s') may be formally written as an integral over all incident directions within the system NA as:

$$I(s')=|\int P \cdot \mathbb{R}(s',s) \cdot A(s) ds|^2 = |\mathbb{R} P \langle |A \rangle|^2, \quad (1)$$

where A is the input polarization, P is the analyzer's transmitted polarization, and the angular brackets are a shorthand for the dot products and the integral over directions of incidence. In practice, the problem is treated with a set of discrete input and output directions, and one may therefore treat A and P as vectors and as a discrete matrix that connects not only polarizations but also input and output propagating orders. While either A or P could, in principle, vary with direction, we choose a fixed analyzer and allow A to vary. For a null measurement, the task would be to deduce an input polarization such that I(s')=0 over the entire pupil. An off-null measurement will deviate from the null condition.

We suppose that the scattering matrix may be expanded in a Taylor series for small variations in a selection of process parameters $p_n$ as:

$$R(s', s) = R_0(s', s) + \sum_{n=1}^{N} p_n R_n(s', s). \quad (2)$$

In (1), each $p_n$ represents the deviation from a nominal value, so that $$I(s', p_1, p_2, \ldots) == \left|\langle P|R_0|A\rangle + \sum_{n=1}^{N} p_n \langle P|R_n|A\rangle\right|^2. \quad (3)$$

For a null measurement, we would require I=0 across the pupil for a sample with no process errors ($p_n$=0). For an off-null measurement, we seek an input polarization distribution A that satisfies the constraint $$\langle P|R_0|A\rangle == -\sum_{n=1}^{N} \overline{p}_n(s')\langle P|R_n|A\rangle. \quad (4)$$

where the functions $p_n^{bar}$ (s') are real. The magnitude of these functions will determine the dynamic range of the measurement; their shape will determine the input polarization while attempting to distinguish different parameters. The irradiance in the pupil will then vary in a systematic way with each process parameter as:

$$I(s') = \left|\sum_{n=1}^{N}(p_n - \overline{p}_n(s'))\langle P|R_n|A\rangle\right|^2. \quad (5)$$

The goal, then, is to seek an input polarization distribution that yields a desirable functional form of each $p_n^{bar}$(s')

Simplification for a Structure with No Macropitch

A structure with no macropitch will have the property $\langle P|\mathbb{R}|A = P \cdot \mathbb{R}(s') \cdot A^*(s')$, where the scattering matrix simply couples between polarizations. The constraint in equation (4) then reduces to the condition $$P \cdot \left(R_0 + \sum_{n=1}^{N} \overline{p}_n R_n\right) \cdot A^* = 0. \quad (6)$$

For the structure without a macropitch, the input polarization may then be related to the input complex amplitude in the following fashion:

$$A(s) == \begin{bmatrix} 0 & 1 \\ -1 & 0 \end{bmatrix} \cdot \left[R_0 + \sum_{n=1}^{N} \overline{p}_n R_n\right] \cdot P^* A(s), \quad (7)$$

in which A(s) is the input amplitude distribution and can be chosen suitably. Once we choose A(s) and the functions $p_n^{bar}$(s'), the incident angular spectrum is determined.

Distinguishing Between Process Parameters

Our goal is to choose $p_n^{bar}$(s') so that the measured pupil irradiance provides the most information about the process parameters. To do so, we examine the variation in pupil irradiance with small changes in process parameter. Differentiating (3) yields $$\frac{\partial I}{\partial p_n}(s', p_1, p_2, \ldots) = 2\sum_{n'=1}^{N}(p_{n'} - \overline{p}_{n'}(s'))\Gamma_{n,n'}(s'), \quad (8)$$

where $$\Gamma_{n,n'}(s') = \mathbb{R}\{Tr[P \cdot R_n^* \cdot A \cdot R_{n'}]\}. \quad (9)$$

For M measured points in the pupil, equation (8) can be represented as an M×N matrix that has a nonzero singular value for each of the N separable process parameters. In practice, the functions $p_n^{bar}$ should then be chosen so that these singular values are flat, similar, and as large as possible. This will maximize the information that can be obtained from a single irradiance measurement.

Example Computation

In the following example, we consider a sample with 100 nm deep trenches having 102 nm pitch and a 50% duty cycle that can incur errors in critical dimension, sidewall angle, oxide thickness, or etch depth. The procedure is as follows: We first use RCWA to compute scattering matrices for the nominal structure and for structures with combinations of the four process errors. The ranges are: ±1 degree for sidewall angle; ±1 nm in feature width (CD) and etch depth; and oxide layer from 0-10 nm with a 5 nm nominal thickness. For this simple example we chose orthogonal sinusoidal functions as shown in FIG. 7

Figure 7:
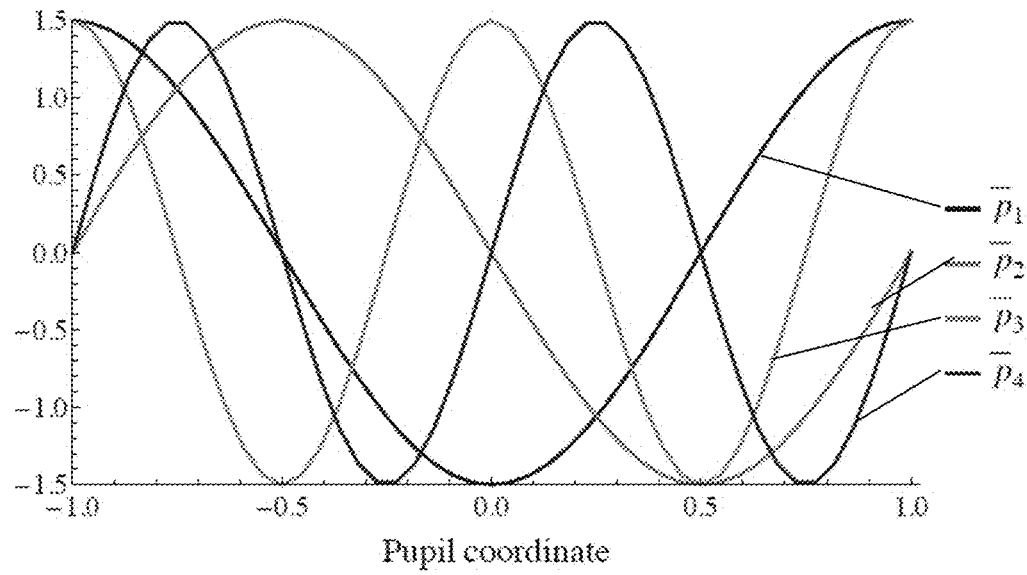
FIG. 7 graphically illustrates the $p_n^{bar}$ functions chosen for the measurement/characterization of four different process error parameters: $p_1^{bar}$—sidewall angle; $p_2^{bar}$—feature width (CD); $p_3^{bar}$—etch depth; $p_4^{bar}$—oxide layer, according to an exemplary aspect of the invention.
Figure 8:
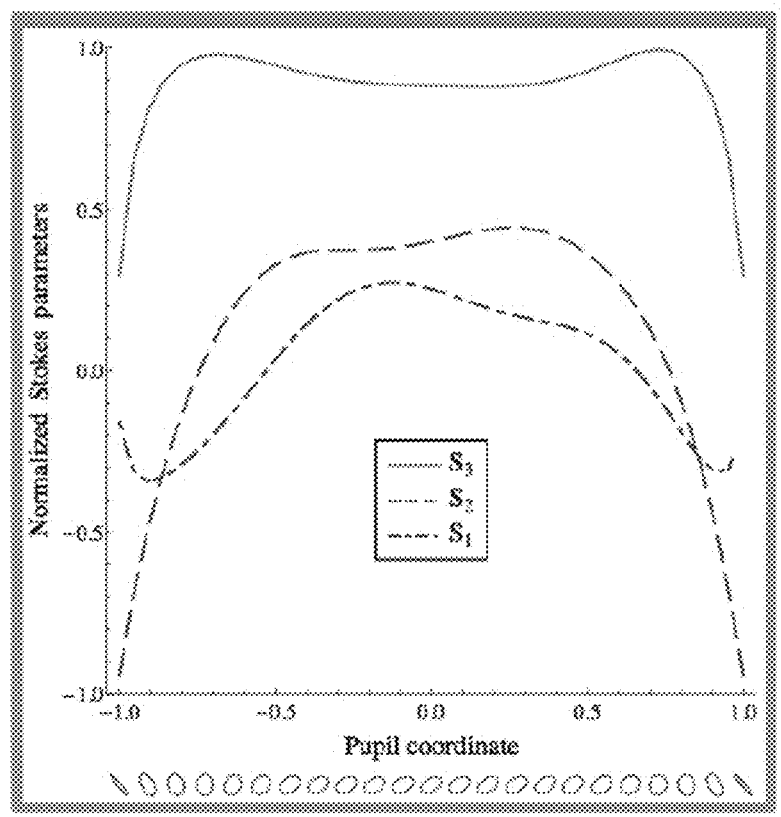
FIG. 8 graphically illustrates the Normalized Stokes parameters for the input fields required to produce the parameter functions shown in FIG. 7. The graphic below the horizontal axis illustrates the polarization ellipse for each point in the pupil.

FIG. 8 shows the irradiance profile and the (normalized) Stokes parameters required for the functional forms of FIG. 7. The discontinuities in the polarization profile appear at the zeros of the pupil amplitude; a practical modification would be to smooth the profile near the zeros. There is significant energy and also sharp polarization changes near the edge of the pupil. Any experimental implementation of this approach would likely use polarization controllers such as liquid crystal spatial light modulators; the ability of the particular devices to achieve both amplitude modulation and complete polarization control is important. We have recently reported on a liquid crystal device that could do this in M. J. Theisen, S. T. Head, T. G. Brown, S. R. Gillmer, J. D. Ellis, "Amplitude, phase, and polarization control with a single spatial light modulator." Proc. SPIE 8949, 8949-69 (2014).

Parameter Recovery

Figure 9:
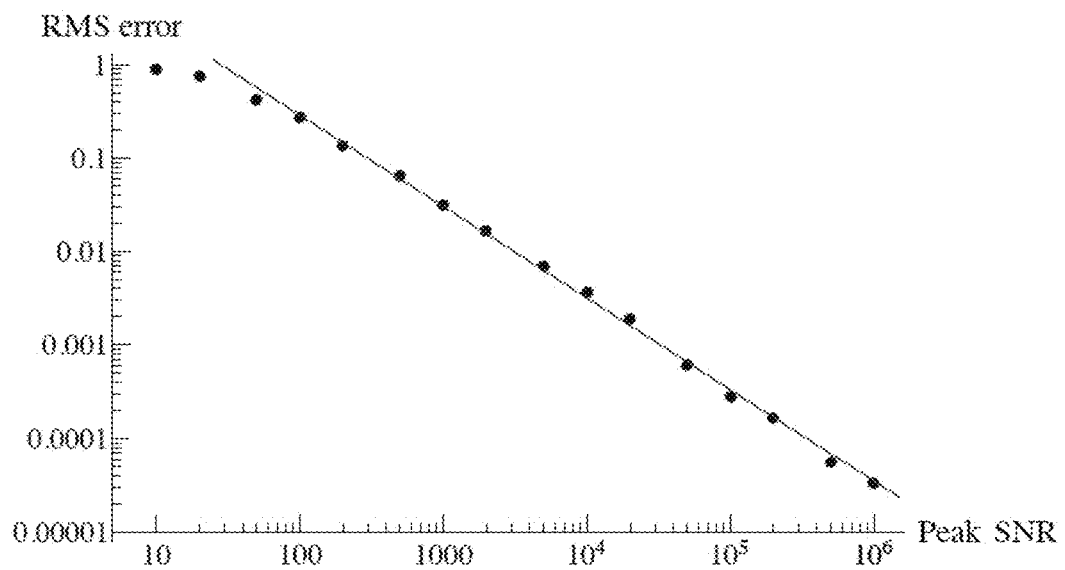
FIG. 9 graphically illustrates the average parameter retrieval error for the examples of FIG. 7.

We first consider an ideal situation (free of noise), in which the parameters are recovered by a least-squares optimization algorithm. The typical numerical errors were about a factor of $10^{-7}$ smaller than the parameter retrieval range. The procedure was then tested using a Poisson noise model, with the results as shown in FIG. 9, in which the vertical axis represents the (normalized) mean of the rms error over 1000 realizations.

Table 1 shows a comparison of predicted errors for the four process parameters shown in FIG. 7 based on 1000 trials using two different noise models and peak signal to noise ratios of 1000 and 100. The results clearly show that retrieval of this sort is robust against ordinary noise sources and that the embodied method could be employed for multiparameter retrieval for very small features.

TABLE 1

Parameter retrieval errors for the parameters of FIG. 4, compared for two different noise models.

| Parameter | Without noise | Gaussian noise (SNR = 100) | Gaussian noise (SNR = 1000) | Poisson noise (SNR = 100) | Poisson noise (SNR = 1000) |
| --- | --- | --- | --- | --- | --- |
| Wall angle (°) | $2.01 \times 10^{-7}$ | 0.2423 | 0.0280 | 0.1918 | 0.0229 |
| Duty cycle (width in nm) | $9.40 \times 10^{-7}$ | 0.1118 | 0.0128 | 0.0927 | 0.0114 |
| Height (nm) | $1.63 \times 10^{-6}$ | 0.2002 | 0.0230 | 0.1552 | 0.0183 |
| Oxide layer (nm) | $2.57 \times 10^{-6}$ | 0.3088 | 0.0352 | 0.2639 | 0.0326 |

The embodied method does not have intrinsic resolution limitations. To illustrate this point, the scattering calculations and the recovery algorithms described above were modeled at a wavelength of 1 µm, about 20 times longer than the smallest feature size and more than 1000 times longer than the estimated minimum detectable CD error. We believe that parameter recovery using near infrared wavelengths will be especially important for deep trench structures and for probing doping-dependent shifts of the silicon band edge. The use of multiple wavelengths near the band edge could assist in such difficult tasks as decoupling line edge roughness and oxide layer thickness.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. A focused beam scatterometry method for characterizing an object having a periodic or quasi-periodic structure and one or more process errors, comprising:
   selecting a predictive scattering model for a perfectly specified test target of the object for providing predictive data;
   identifying one or more process error parameters of the object to be characterized;
   providing a focused light field input having at least a spatially varying polarization distribution over the field that will yield a particular functional form output for a respective one of the process errors, given a known polarization output analyzer;
   illuminating the object or a test target of the object with the input light field;
   collecting light scattered/reflected from the object or the test target of the object as measured data; and
   characterizing each of the identified one or more process error parameters in a single measurement by comparing the measured data with the predictive data.

2. The method of claim 1, wherein the one or more process error parameters include a process error and a measurement range.

3. The method of claim 1, further comprising selecting the spatially varying polarization distribution of the input light field that will yield a particular functional form output for at least two respective ones of the process errors.

4. The method of claim 1, further comprising selecting the spatially varying polarization of the input light field that will yield a particular functional form output for at least four respective ones of the process errors.

5. The method of claim 1, wherein the one or more process error parameters are selected from a group consisting of an etch depth, a side wall angle, a coating thickness, a coating composition, a line edge roughness, and a critical dimension of the object.

6. The method of claim 1, wherein at least one of the one or more process error parameters has a scale less than 1000 nanometers.

7. The method of claim 6, wherein the at least one of the one or more process error parameters has a scale less than 22 nanometers.

8. The method of claim 1, wherein the input light field is in the form of a single focused beam comprising an ensemble of plane waves.

9. The method of claim 8, wherein each of the plane waves has an intensity, a polarization, and a phase characteristic, further wherein at least some of the waves' characteristics are different than at least some others of the waves' characteristics.

10. The method of claim 1, wherein collecting the light scattered/reflected from the object or the test target of the object comprises measuring an irradiance distribution of the scattered/reflected light over an exit pupil of a measurement system used for the measurement.

11. The method of claim 1, wherein the object is a semiconductor fabrication.

12. The method of claim 11, wherein the object is a Fin FET device.

13. The method of claim 1, further comprising collecting the measured data using an off-null methodology.

14. The method of claim 13, wherein the off-nulling conditions for the parameters are varied over the pupil of the system, such that the final irradiance distributions have shapes from which the error parameters can be inferred.

15. A focused beam scatterometry system for characterizing an object having a periodic or quasi-periodic structure and one or more process errors, comprising:
   an input light field polarization coding component;
   a focusing component for focusing the input light field on an object to be characterized, disposed in an optical path of the polarization coding component;
   a polarization analyzer component disposed to receive the input light field scattered/reflected from the object to be characterized; and
   a detector disposed to receive an output from the polarization analyzer.

16. The system of claim 15, wherein the input light field polarization coding component is a spatial light modulator (SLM).

17. The system of claim 15, wherein the polarization analyzer component is one of a linear polarizer and a circular polarizer.

18. The system of claim 15, comprising an off-null configuration.

* * * * *